(12) United States Patent
Di Marco et al.

(10) Patent No.: US 11,484,669 B2
(45) Date of Patent: Nov. 1, 2022

(54) MICROFLUIDIC DISPENSER DEVICE FOR DELIVERING INHALABLE SUBSTANCES

(71) Applicant: STMICROELECTRONICS S.R.L., Agrate Brianza (IT)

(72) Inventors: Oriana Rita Antonia Di Marco, Milan (IT); Domenico Giusti, Caponago (IT)

(73) Assignee: STMICROELECTRONICS S.r.l., Agrate Brianza (IT)

( * ) Notice: Subject to any disclaimer, the term of this patent is extended or adjusted under 35 U.S.C. 154(b) by 715 days.

(21) Appl. No.: 16/408,362

(22) Filed: May 9, 2019

(65) Prior Publication Data
US 2019/0350260 A1 Nov. 21, 2019

(30) Foreign Application Priority Data

May 15, 2018 (IT) .......................... 102018000005372

(51) Int. Cl.
| | |
|---|---|
| *A61M 11/04* | (2006.01) |
| *A61M 15/06* | (2006.01) |
| *H05B 3/42* | (2006.01) |
| *A24F 40/30* | (2020.01) |
| *A24F 40/46* | (2020.01) |
| *A24F 40/485* | (2020.01) |
| *A24F 40/10* | (2020.01) |

(52) U.S. Cl.
CPC ........... *A61M 11/042* (2014.02); *A24F 40/30* (2020.01); *A24F 40/46* (2020.01); *A24F 40/485* (2020.01); *A61M 15/06* (2013.01); *H05B 3/42* (2013.01); *A24F 40/10* (2020.01)

(58) Field of Classification Search
CPC ..... A61M 11/042; A61M 15/06; A24F 40/46; A24F 40/485; A24F 40/30

USPC ......................................................... 131/329
See application file for complete search history.

(56) References Cited

U.S. PATENT DOCUMENTS

| | | | |
|---|---|---|---|
| 6,684,880 B2 * | 2/2004 | Trueba | A61M 15/025 128/200.19 |
| 6,702,894 B2 * | 3/2004 | Lee | B41J 2/04 118/325 |

(Continued)

FOREIGN PATENT DOCUMENTS

CN 205461048 U 8/2016

OTHER PUBLICATIONS

Hawkins, Bill et al., "Vibrating Mesh Nebulizer Reference Design", Microchip Technology Inc., AN2265, 2016-2017, 50 pages.

*Primary Examiner* — Alexander Gilman
(74) *Attorney, Agent, or Firm* — Seed IP Law Group LLP

(57) ABSTRACT

A microfluidic dispenser device of inhalable substances includes a casing, housed in which are a driving circuit and a microfluidic cartridge having a tank that contains a liquid to be delivered. The microfluidic cartridge is provided with at least one nebulizer controlled by the driving device. The nebulizer includes: a substrate; a plurality of chambers formed on the substrate and fluidically coupled to the tank for receiving the liquid to be delivered; and a plurality of heaters, which are formed on the substrate in positions corresponding to respective chambers, are thermally coupled to the respective chambers and are separated from the respective chambers by an insulating layer, and are controlled by the driving device. Each chamber is fluidically connected with the outside by at least one respective nozzle.

22 Claims, 8 Drawing Sheets

(56) References Cited

U.S. PATENT DOCUMENTS

Figure 1:
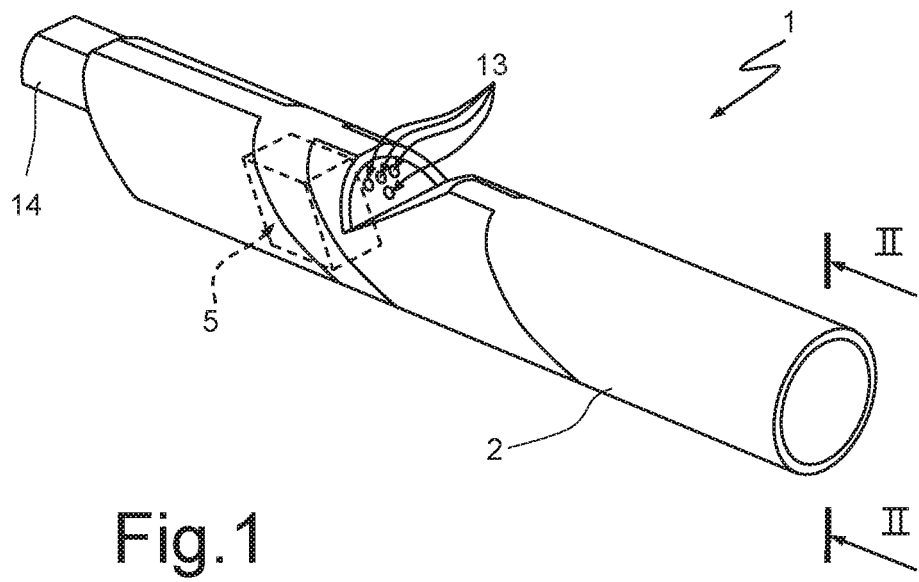

| | | | | |
|---|---|---|---|---|
| 7,469,696 | B2* | 12/2008 | Yang | A61M 15/025 128/200.14 |
| 7,726,303 | B2* | 6/2010 | Tyvoll | A61M 15/025 128/200.21 |
| 8,596,262 | B2* | 12/2013 | Terai | A61M 15/02 128/200.14 |
| 8,721,910 | B2* | 5/2014 | Merassi | B05B 17/0638 438/689 |
| 9,174,445 | B1* | 11/2015 | Prati | B41J 2/14427 |
| 10,172,388 | B2* | 1/2019 | Sears | A24F 40/485 |
| 2003/0186474 | A1* | 10/2003 | Haluzak | B41J 2/1629 438/782 |
| 2005/0150489 | A1* | 7/2005 | Dunfield | A61P 25/34 128/200.14 |
| 2006/0060191 | A1* | 3/2006 | Yang | A61M 15/0065 128/200.14 |
| 2009/0260624 | A1* | 10/2009 | Wada | A61M 15/00 128/203.12 |
| 2010/0288270 | A1* | 11/2010 | Wada | B41J 2/1433 128/200.14 |
| 2015/0114409 | A1* | 4/2015 | Brammer | A61M 15/025 392/394 |
| 2018/0036763 | A1* | 2/2018 | Giusti | B05D 1/02 |
| 2018/0141074 | A1* | 5/2018 | Giusti | B41J 2/1433 |

* cited by examiner

MICROFLUIDIC DISPENSER DEVICE FOR DELIVERING INHALABLE SUBSTANCES

BACKGROUND

Technical Field

The present disclosure relates to a microfluidic dispenser device for delivering inhalable substances.

Description of the Related Art

As is known, the need to control precisely delivery of inhalable substances, both for therapeutic purposes and for the production of non-medical devices, such as the so-called electronic cigarettes, has led to the development of miniaturized delivering devices that are easy to use.

A dispenser device of inhalable substances of a known type normally comprises a tank, which contains a fluid with the substances to be delivered in solution, and at least one delivery chamber, provided with ejector nozzles and supplied by the tank. An actuator housed in the chamber driven by a control device causes expulsion of a controlled amount of fluid.

Currently, in particular in electronic cigarettes, actuators of a resistive or inductive type are mainly used.

In resistive actuators, a resistive electrode is placed within the chamber and is wound, in contact, around a spongy cylindrical body, also referred to as "wick", which is generally made of glass fiber. The electrode traversed by current heats the fluid to be delivered up to boiling point, and the formation of bubbles causes expulsion of corresponding volumes of fluid to be delivered. Control of delivery is generally based upon flowmeters that detect the flow rate of fluid coming out of the chamber. Delivery devices of this sort suffer from certain limitations. In the first place, the electrode is directly in contact with the fluid to be delivered, and this may lead to release of undesirable and potentially harmful substances. Moreover, the entire volume of fluid present in the chamber is brought to boiling point and hence reaches rather high temperatures. Such a condition may trigger reactions in the fluid that alter the substances to be delivered. If the substances to be delivered are drugs, the reactions may render the active principles inefficacious. If, instead, the device delivers surrogates of smoke, the organoleptic characteristics may be degraded. In the worst scenarios, the reactions due to the high temperature may produce harmful substances that are inhaled to the detriment of the user. A further limit of known devices is the low precision in controlling the doses of inhalable substances delivered.

In actuators of an inductive type, a coil is wound around the wick, at a distance. The coil traversed by current remains relatively cold, but generates a magnetic field that heats the spongy body and the liquid until it causes expulsion of the latter. Actuators of this type do not present problems linked to the release of substances from the coil (which is not in contact with the liquid) and to the excessive heating, but are costly and not suited to being integrated in disposable cartridges, as would be preferable.

BRIEF SUMMARY

At least one embodiment of the present disclosure is a microfluidic dispenser device for delivering inhalable substances that will enable at least some of the limitations described above to be overcome or at least mitigated.

According to the present disclosure, a microfluidic dispenser device for delivering inhalable substances is provided.

BRIEF DESCRIPTION OF THE SEVERAL VIEWS OF THE DRAWINGS

For a better understanding of the disclosure, some embodiments thereof will now be described, purely by way of non-limiting example and with reference to the attached drawings, wherein:

FIG. 1 is a perspective view of a microfluidic dispenser device of inhalable substances according to an embodiment of the present disclosure;

FIG. 2 is a perspective view of the microfluidic delivery device of FIG. 1, sectioned along the plane II-II of FIG. 1;

FIG. 3 is a perspective view of a microfluidic cartridge used in the microfluidic delivery device of FIG. 1;

FIG. 4A is a side view of the microfluidic cartridge of FIG. 3, sectioned along the plane Iv-Iv of FIG. 3;

FIG. 4B is a side view of a microfluidic cartridge in accordance with a different embodiment of the present disclosure;

FIG. 5 is a perspective view of a component of the microfluidic cartridge of FIG. 3;

FIG. 6 is an exploded perspective view of the component of FIG. 5;

FIG. 7 is an enlarged perspective view of a portion of the component of FIG. 5, with parts removed for clarity;

FIG. 8 is a top plan view of an enlarged detail of the component of FIG. 5;

FIG. 9 is a perspective view of the detail of FIG. 8, sectioned along the plane IX-IX of FIG. 8;

FIG. 10 is a perspective view of a detail of a component of a microfluidic cartridge that can be used in a microfluidic delivery device according to a different embodiment of the disclosure;

FIG. 11 is a perspective view of a detail of a component of a microfluidic cartridge that can be used in a microfluidic delivery device according to a further embodiment of the disclosure;

FIG. 12 is a perspective view of a detail of a component of a microfluidic cartridge that can be used in a microfluidic delivery device according to a further embodiment of the disclosure;

FIGS. 13A-13E illustrate operation of the component of FIG. 5;

FIG. 14 is a perspective cross-sectional view of a component of a microfluidic cartridge that can be used in a microfluidic delivery device according to a further embodiment of the disclosure;

FIG. 15 is a top plan view of an enlarged detail of the component of FIG. 14; and FIG. 16 is a schematic lateral sectional view of a microfluidic delivery device according to a further embodiment of the disclosure.

DETAILED DESCRIPTION

With reference to FIGS. 1 and 2, number 1 designates as a whole a microfluidic dispenser device for delivering inhalable substances, which in the embodiment illustrated is an electronic cigarette. The microfluidic delivery device 1 comprises a casing 2, housed within which are a driving device 3, a battery 4, and a disposable microfluidic cartridge 5.

In greater detail, the casing 2 comprises an elongated tubular body 6 made of polymeric and/or metal material, and includes a control housing 7 and a cartridge housing 8. In one embodiment, the control housing 7 defines a substantially axial blind cavity 7A, which is open at a first end 2a of the casing 2 and may be closed, for example, with an appropriately designed lid (not illustrated). The driving device 3 may be welded on a support 10, for example a PCB (printed circuit board) that may be inserted in the cavity 7A in the control housing 7 together with the battery 4.

The cartridge housing 8 encloses a chamber 8A set between the control housing 7 and a second end 2b of the casing 2 and accessible through a hatch 11 for insertion and removal of the cartridges 5. The chamber 8A in the cartridge housing 8 communicates with the outside through inlet holes 13 and a mouthpiece 14 for release of the inhalable substance. More precisely, the inlet holes 13 and the mouthpiece 14 are arranged so that suction through the mouthpiece 14 will draw air into the chamber 8A through the inlet holes 13, passage of the air through the chamber 8A, and subsequent release through the mouthpiece 14.

Electrical connection lines 15 are embedded in the casing 2 and extend between the cavity 7A and the chamber 8A for electrically coupling the driving device 3 and the microfluidic cartridge 5 that is located in the chamber 8A.

Figure 2:
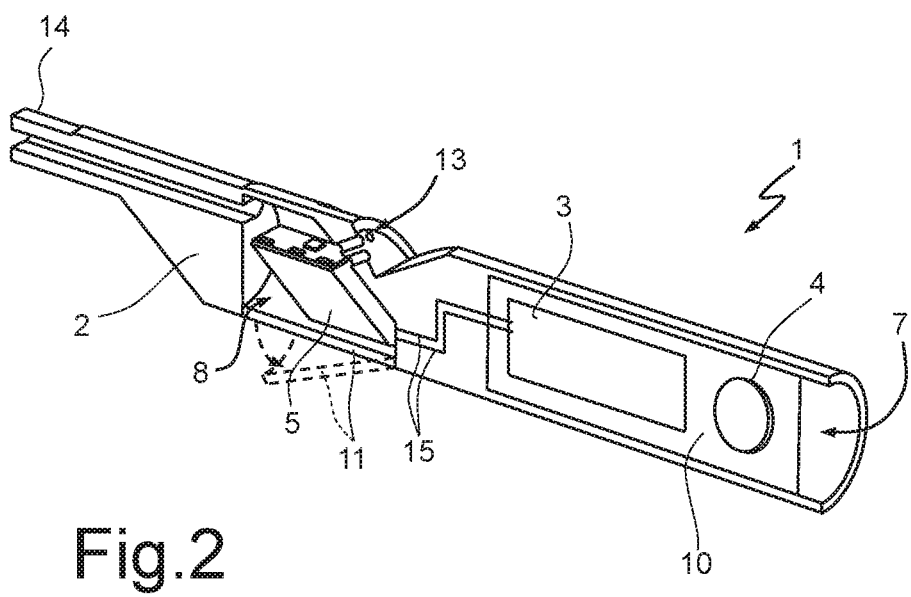
Figure 3:
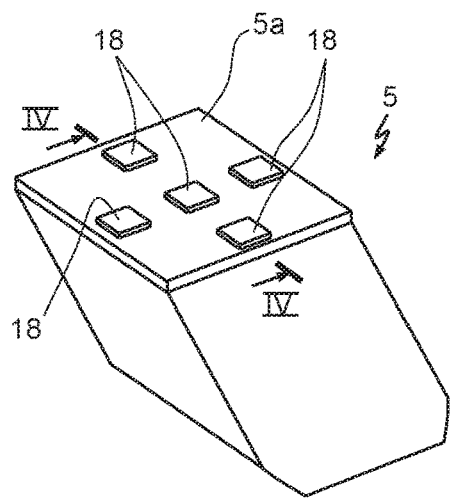
Figure 4A:
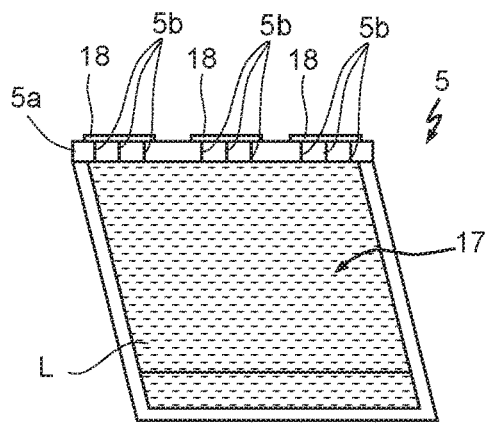
Figure 4B:
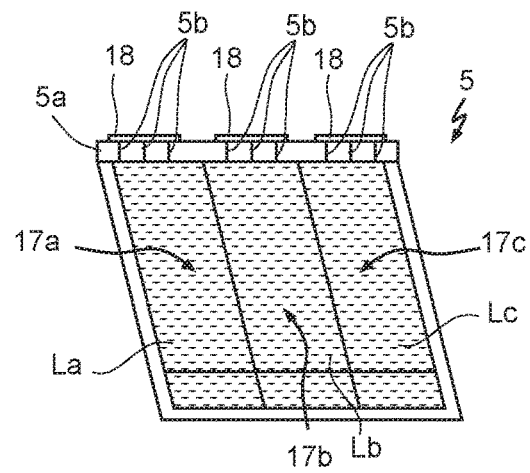
Figure 5:
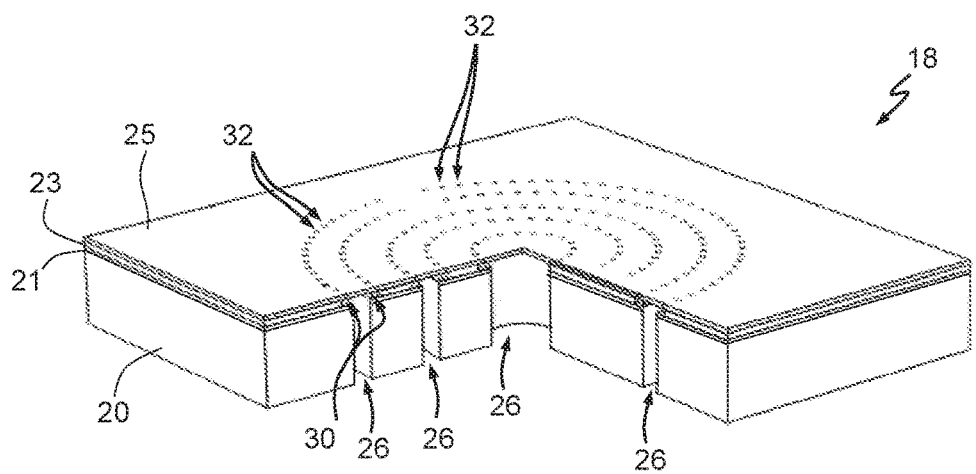
Figure 6:
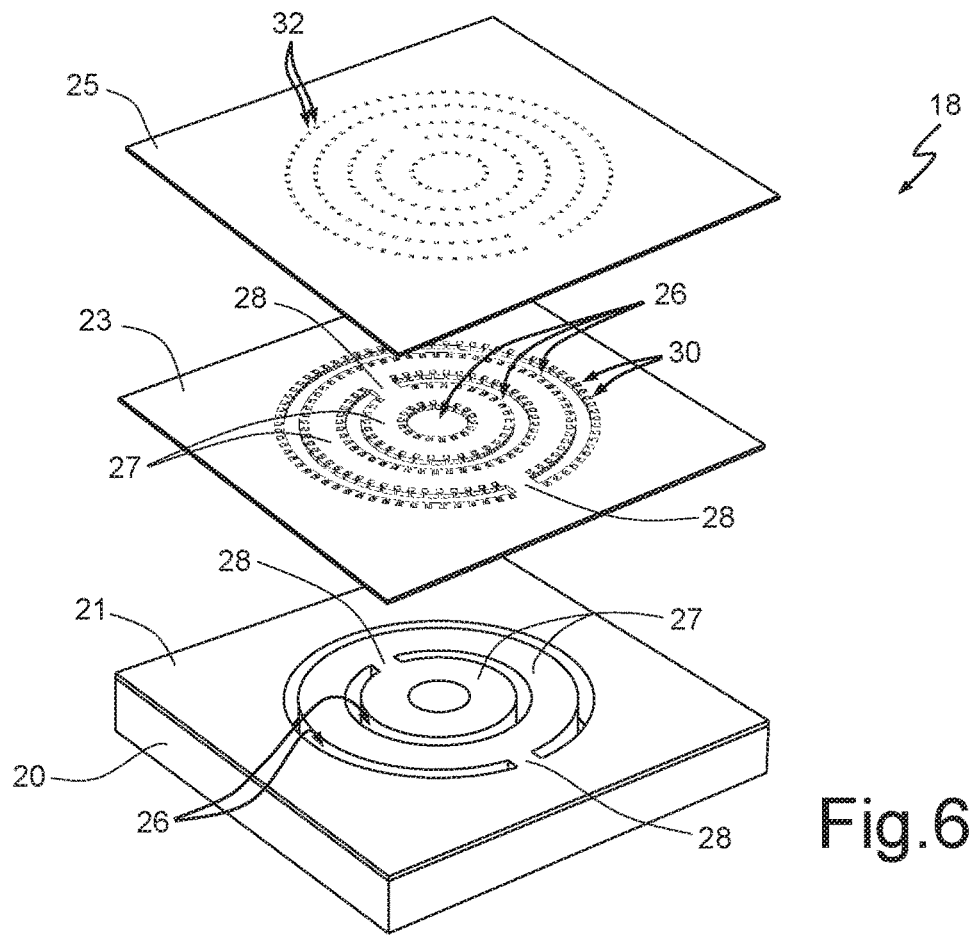
Figure 7:
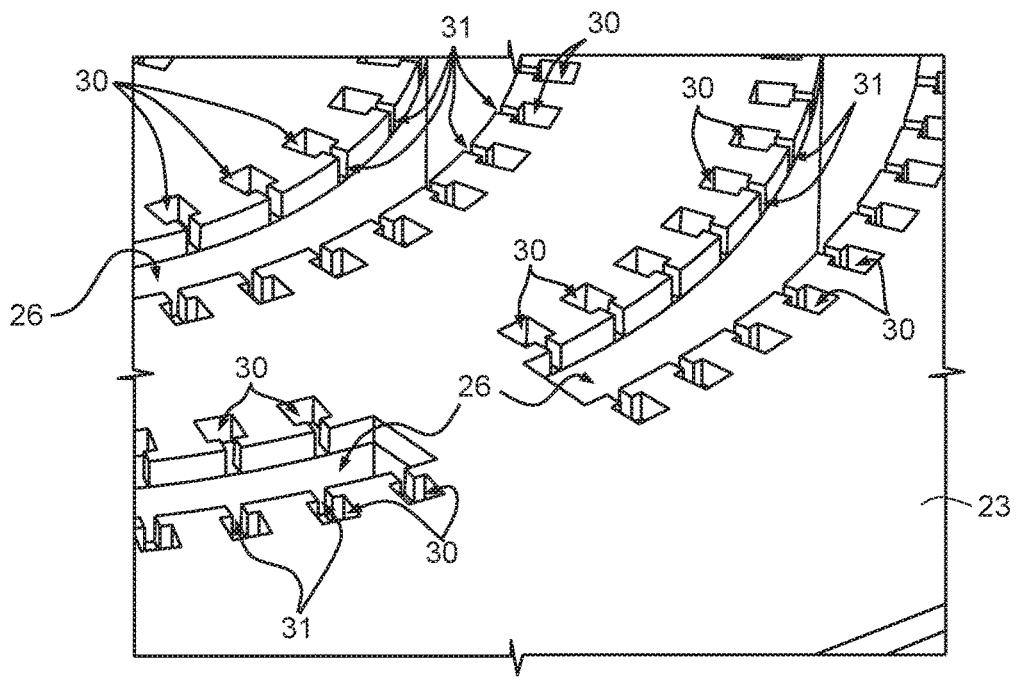
Figure 8:
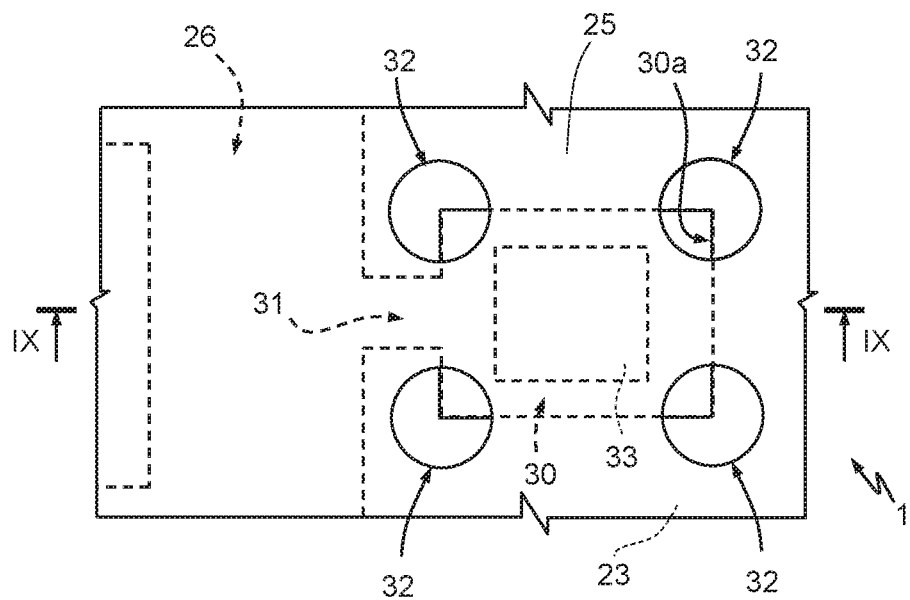
Figure 9:
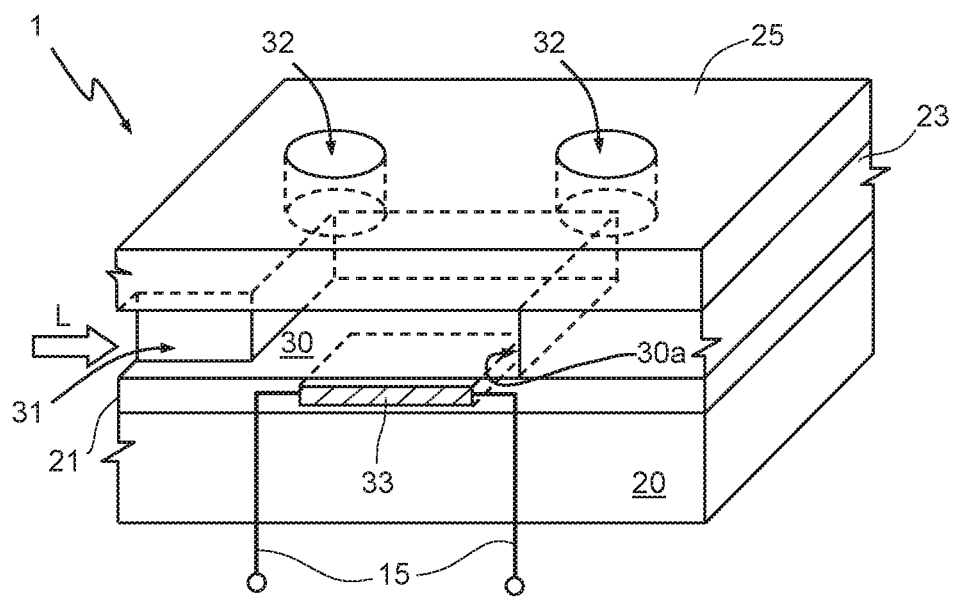
Figure 10:
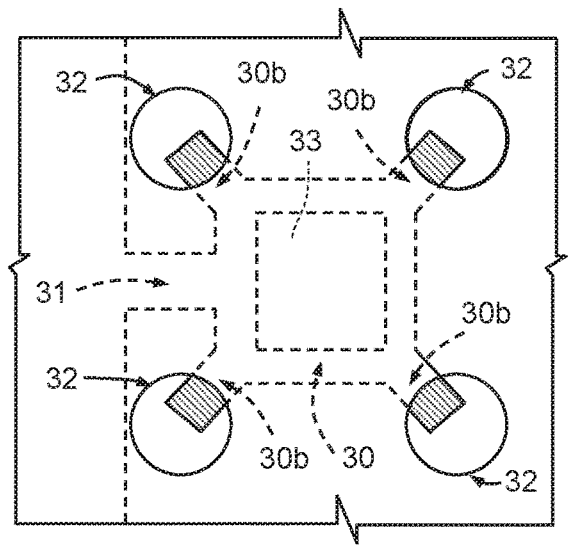
Figure 11:
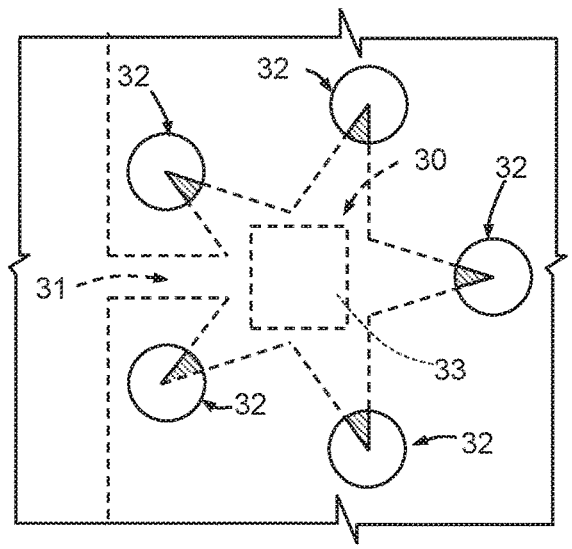
Figure 12:
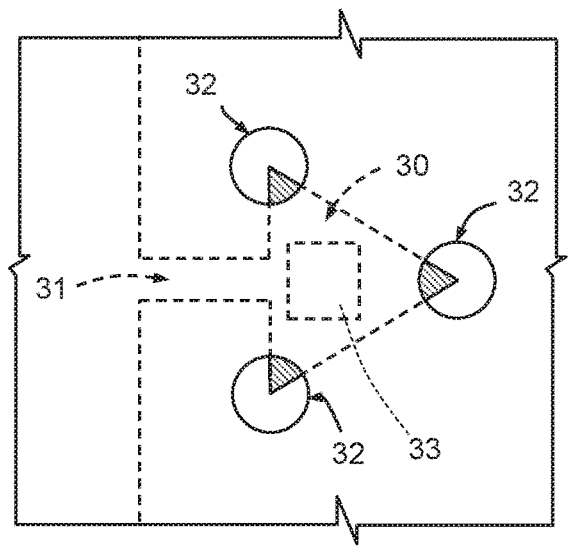

FIGS. 3 and 4A illustrate an example of microfluidic cartridge 5, which comprises a tank 17, containing a liquid L that includes a substance to be delivered, and a plurality of nebulizers 18 controlled by the driving device 3. The nebulizers 18 are bonded to an outer face of a lid 5a of the microfluidic cartridge 5, defined, for example, by a PCB and provided with through channels 5b for fluidic coupling of the nebulizers 18 to the tank 17. In the example of FIGS. 3 and 4A, in particular, the microfluidic cartridge 5 comprises five nebulizers 18 arranged in criss-cross fashion. The number and arrangement of the nebulizers 18 may, however, vary according to design preferences. In one embodiment, even just one nebulizer 18 may be present.

In an alternative embodiment, to which FIG. 4B refers, the microfluidic cartridge 5 comprises a plurality of tanks, for example three tanks 17*a*-17*c*, separated from each other and containing respective liquids La-Lc with respective distinct substances to be delivered. Each tank 17*a*-17*c* is fluidly coupled with a respective nebulizer 18 or group of nebulizers 18, distinct from nebulizers 18 or groups of nebulizers 18 of the other tanks. In this way, it is possible to deliver several substances at the same time with controlled doses of each. The number and size of the tanks, as well as the type and number of substances to be delivered, may be selected according to project preferences.

FIGS. 5 and 6 show in greater detail one of the nebulizers 18. It is understood that the other nebulizers 18 have the same structure as the one illustrated. In other embodiments, however, the nebulizers could differ as regards some details, such as the number and distribution of the ejection nozzles (described in greater depth hereinafter). As may be appreciated more fully from the exploded view of FIG. 6, the nebulizer 18 comprises a substrate 20, covered by an insulating layer 21, a chamber layer 23, which extends over the insulating layer 21, and a nozzle plate 25 bonded to the chamber layer 23. The substrate 20, the insulating layer 21, and the chamber layer 23 may, for example, be made, respectively, of semiconductor material, silicon oxide or silicon nitride, and a polymeric material, such as dry film. The nozzle plate 25 may be made of the same material that forms the chamber layer 23 or of semiconductor material.

Supply passages 26 fluidically coupled to the tank 17 are provided through the substrate 20, the insulating layer 21, and the chamber layer 23. In one embodiment, the supply passages 26 are circular and concentric and define annular frame regions 27 comprising respective portions of the substrate 20, of the insulating layer 21, and of the chamber layer 23, which are also concentric. In the embodiment illustrated in FIGS. 5 and 6, in particular, two outer supply passages 26 define two frame regions 27 and separate them from the rest of the substrate 20. The innermost supply passage 26 is arranged at the center. Bridges 28 connect the frame regions 27 to one another and the outermost frame region 27 to the substrate 20.

It is, however, understood that the shape and number of the supply passages (and consequently of the substrate portions adjacent to the openings) may be freely defined according to the design preferences. By way of non-limiting example, the supply passages could have a generally polygonal or else rectilinear shape and be parallel to one another.

Chambers 30 are formed in the chamber layer 23 along the supply passages 26, as illustrated also in FIG. 7. In the embodiment illustrated, the chambers 30 are aligned along the inner and outer edges of the supply passages 26 and are evenly distributed. Moreover, the chambers 30 are fluidically coupled to the supply passages 26 through respective microfluidic channels 31 and are delimited by the insulating layer 21 and, on the side opposite to the substrate 20, by the nozzle plate 25.

FIGS. 8 and 9 illustrate in greater detail one of the chambers 30. In the non-limiting example illustrated, all the chambers 30 have the same shape, structure, and size.

The chamber 30 has a parallelepipedal shape with an approximately rectangular base and is delimited laterally by walls 30*a* that define a lateral surface of the chamber 30 itself.

The chamber 30 is provided with nozzles 32 formed in the nozzle plate 25 in positions corresponding to respective corners of the chamber 30, so that portions of the surfaces of the walls 30*a* extend through the base area of the nozzles 32. The access to the nozzles 32 from the chamber 30 is hence partially obstructed, and the section of passage is a fraction of the base area of the nozzles 32. In the example illustrated, in particular, the area of the section of passage is approximately one quarter of the base area of the nozzles 32. In an alternative embodiment (not illustrated), both the chambers and the nozzles are provided in the chamber layer. More precisely, the chambers are formed on a first face of the chamber layer facing the substrate and occupy a portion of the thickness of the chamber layer itself. The nozzles extend for the remaining portion of the thickness of the chamber layer, between the respective chambers and a second face of the chamber layer opposite to the first face.

The shape of the chamber 30 and the arrangement of the nozzles 32 are not to be considered binding, but may be provided according to design preferences. Alternative examples, which are in any case non-limiting, of the chamber 30 and of the nozzles 32 are illustrated in FIGS. 10-12 (rectangular chamber 30 with niches 30*b* at the vertices and nozzles 32 partially overlapping the niches 30*b*, FIG. 10; chamber 30 that is star-shaped, with nozzles 32 in positions corresponding to the points of the star shape, FIG. 11; triangular chamber 30, with nozzles 32 at the vertices, FIG. 12).

A heater 33 (FIG. 8) is provided within the insulating layer 21 in a position corresponding to the chamber 30, and forms an actuator. The heater 33 may be made (by way of non-limiting example) of polycrystalline silicon, Al, Pt, TiN, TiAlN, TaSiN, TiW. A portion of the insulating layer 21, having a thickness such as to enable thermal coupling with the chamber 30, coats a face of the heater 33 that faces the chamber 30. Consequently, the heater 33 is separated from the chamber 30 and there is no direct contact between the heater 33 and the liquid present in the chamber 30. In one embodiment (not illustrated), the heater may be coated with a thin layer of an insulating and chemically inert material different from the material that forms the insulating layer 21 so as to obtain in any case thermal coupling with the chamber 30 and separation from the liquid L contained in the chamber 30. The heater 33 is controlled by the driving device 3, to which the heater 33 is connected through the electrical connection lines 15 (FIGS. 1 and 2), illustrated only schematically in FIG. 8. The heater 33 may have an area of approximately 40×40 $\mu m^2$ and generate an energy of, for example, 3.5 $\mu J$, and is able to reach a maximum temperature of 450° C. in 2 $\mu s$.

Figure 13A:
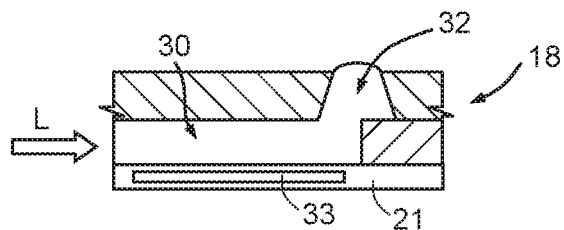
Figure 13B:
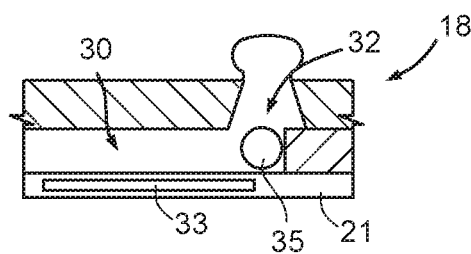
Figure 13C:
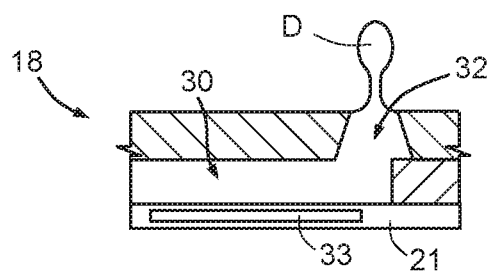
Figure 13D:
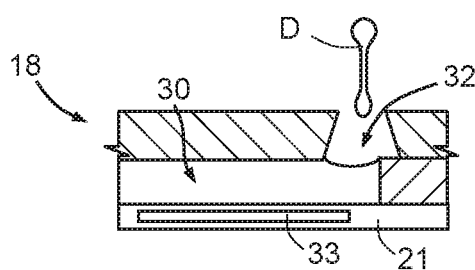
Figure 13E:
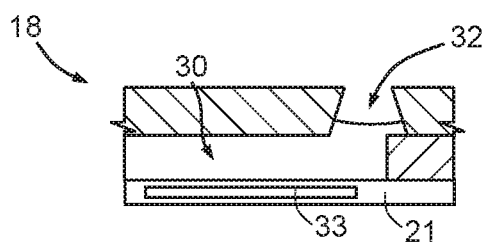

Operation of the nebulizer 18 is illustrated schematically in FIGS. 13A-13E. The liquid L reaches the chamber 30 from the tank 17, passing through the supply passages 26 and the microfluidic channels 31. The heater 33 is activated by the driving device 3 for some microseconds until it reaches a programmed temperature, for example 450° C. In this way, a layer of the liquid L of the thickness of some micrometers is rapidly heated, whereas the temperature of the rest of the liquid L present in the chamber 30 does not vary appreciably, owing to the delay in conduction of heat. The pressure in the layer of liquid L adjacent to the heater 33 increases to a high level, for example approximately 5 atm, to form a vapor bubble 35 (FIG. 13B), which disappears after a few microseconds, for example 10-15 $\mu s$. The pressure thus generated pushes a drop D of liquid 18 through the nozzles 32, as illustrated in FIGS. 13C-13D, and then the liquid L present in the chamber 30 returns to the initial condition (FIG. 13E).

The shape of the nozzles 32 and the area of the section of passage (which is determined by partial overlapping of the nozzles 32 and of the walls 30a of the chamber 30) are selected in such a way that the drops released have a desired diameter. Advantageously, the use of nozzles staggered with respect to the walls of the chambers enables reduction of the area of the sections of passage between the chambers and the nozzles and makes it possible to obtain drops having a very small diameter, as little as 1 $\mu m$, corresponding to a volume of approximately 0.0045 pl, without having to resort to sublithographic processing techniques.

The structure of the nebulizers 18, which can draw advantage from the precision of semiconductor manufacturing techniques, enables an extremely accurate control over the amount of nebulized liquid and, in other words, over the dosage of the substance to be inhaled that is released. Moreover, release is carried out without heating significantly the entire volume of liquid L present in a chamber 30. As has been discussed, in fact, it is sufficient to bring to a high temperature a rather thin layer of liquid L to create a bubble and, consequently, release of a drop. In addition to preventing contamination of the liquid by direct contact with the heater 33, the nebulizers 18 prevent excessive heating from causing reactions that might alter substances present in the liquid L.

The number and arrangement of the chambers 30 and the number and arrangement of the nozzles 32 of each chamber 30 may be selected so as to create a uniform cloud of drops, which is desirable for favoring inhalation of the substances present in the liquid L. This is allowed by the freedom of design offered by the semiconductor manufacturing techniques.

In particular, in the microfluidic delivery device 1 the homogeneity of the cloud of drops favors mixing with the air that is drawn in through the inlet holes 13 and released through the mouthpiece 14.

Figure 14:
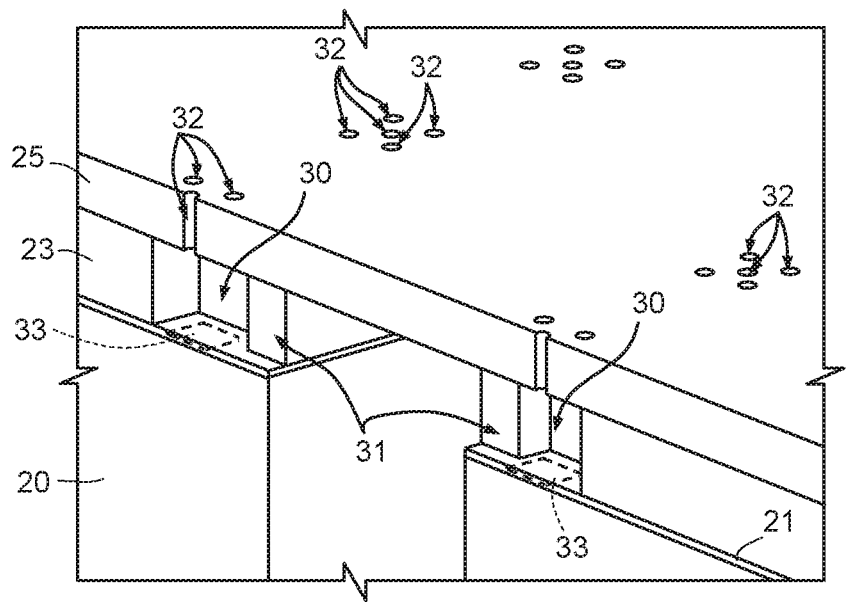
Figure 15:
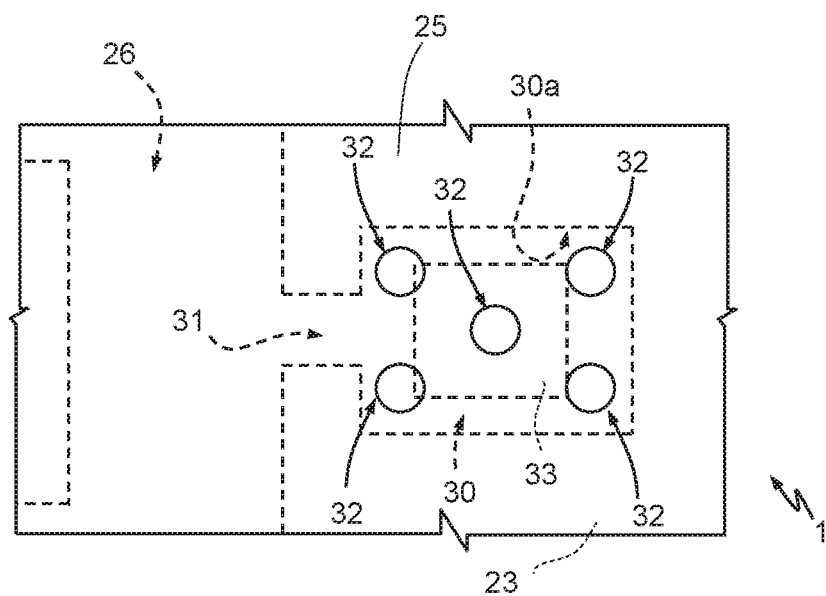

FIGS. 14 and 15 illustrate an alternative example of arrangement of the nozzles 32. In this case, each chamber 30 is provided with five nozzles 32, one of which is aligned to the center of the heater 33.

Figure 16:
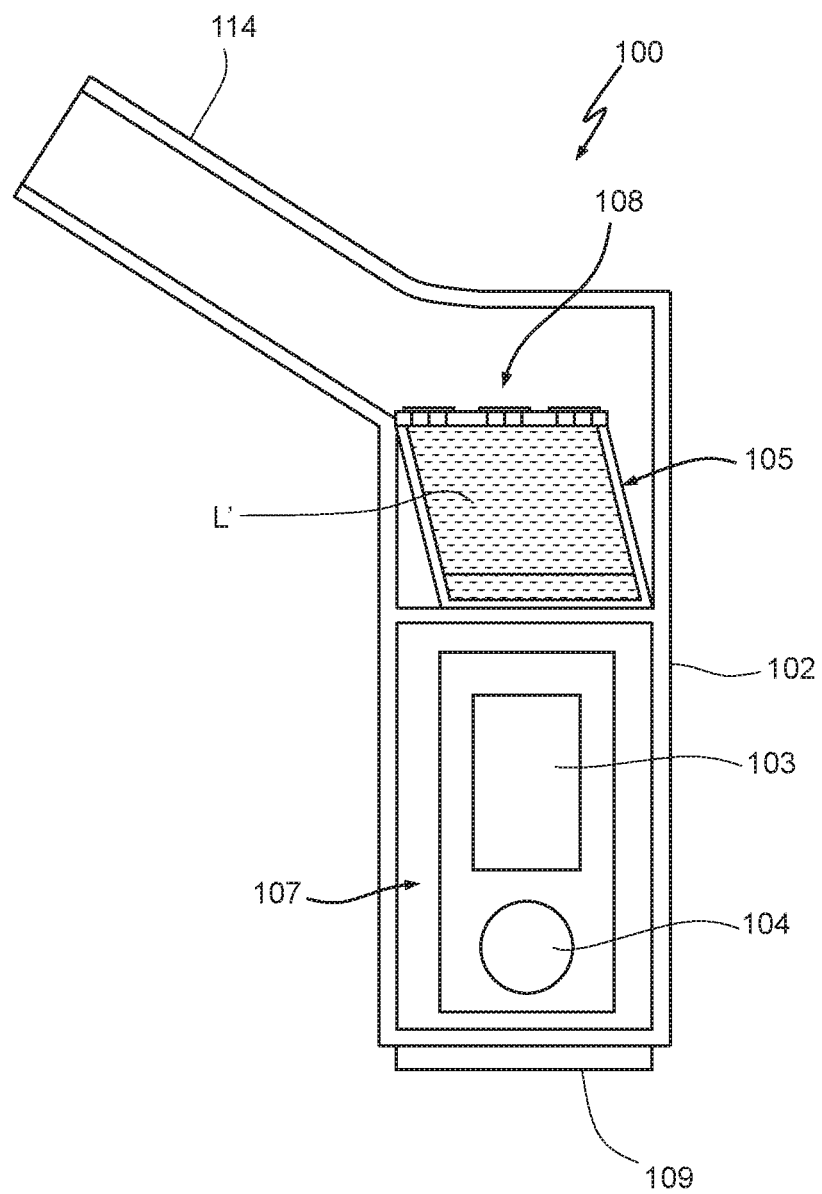

According to a further embodiment (illustrated in FIG. 16), a microfluidic delivery device 100, in particular an inhaler for medicinal substances, comprises a casing 102, housed within which are a driving device 103, a battery 104, and a disposable microfluidic cartridge 105. The driving device 103 and the battery 104 are located in a control housing 107, whereas the microfluidic cartridge 105 is located in a cartridge housing 108. The microfluidic cartridge 105 may be made in accordance with of the examples already described previously and contains a liquid L' in which at least one active principle is dissolved in a controlled concentration.

A control pushbutton 109 enables activation of the driving device 103 and causes release of a controlled amount of liquid L' and, consequently, of an equally controlled dosage of active principle. Release is obtained through a mouthpiece 114 integrated in the casing 102. In the example illustrated, no air-inlet holes are provided, and release of the amount of liquid L' is carried out without pre-mixing with a flow of air.

Finally, it is evident that modifications and variations may be made to the microfluidic dispenser device described herein, without thereby departing from the scope of the present disclosure.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A microfluidic dispenser device for delivering inhalable substances comprising:
   a casing;
   a driving circuit housed in the casing;
   a microfluidic cartridge housed in the casing and having
      a tank and a lid that closes the tank, configured to contain a liquid, and a nebulizer joined to an outer face of the lid and fluidically coupled to the tank via through channels provided in the lid, the nebulizer configured to be controlled by the driving device, the nebulizer including:
      a substrate;
      a plurality of chambers formed on the substrate and fluidically coupled to the tank for receiving the liquid;
      a plurality of heaters formed on the substrate in positions corresponding to the chambers, respectively, wherein the heaters are thermally coupled to the respective chambers, the heaters being configured to be controlled by the driving device;

an insulating layer separating the heaters from the respective chambers;

a plurality of nozzles fluidically connecting the chambers, respectively, to an environment outside of the nebulizer, wherein the chambers are delimited laterally by walls, and portions of surfaces of the walls extend through base areas of at least some of the nozzles.

2. The device according to claim 1, wherein the nebulizer includes a chamber layer on the substrate, the chambers being provided in the chamber layer.

3. The device according to claim 2, comprising a nozzle plate on the chamber layer, the nozzles being provided through the nozzle plate.

4. The device according to claim 3, wherein the chambers are delimited by the insulating layer and, on a side opposite to the substrate, by the nozzle plate.

5. The device according to claim 3, wherein the substrate is made of semiconductor material and the chamber layer is made of a polymeric material.

6. The device according to claim 1, wherein the nebulizer comprises:

microfluidic channels; and supply passages fluidically coupled to the tank and wherein the chambers are fluidically coupled to the supply passages, respectively, by the microfluidic channels, respectively.

7. The device according to claim 6, wherein the chambers are aligned along edges of the supply passages and are evenly distributed.

8. The device according to claim 6, wherein the supply passages are circular and concentric and define annular frame regions that comprise respective portions of the substrate, of the insulating layer, and of the chamber layer and are also concentric.

9. The device according to claim 6, wherein the substrate includes:

first and second frame regions;

first and second outer supply openings, the first outer supply opening separating the first and second frame regions from each other, and the second outer supply opening separating the second frame region from an outer portion of the substrate;

an innermost supply passage is arranged centrally within the first frame region;

a first bridge connecting the first and second frame regions to one another; and a second bridge connecting the second frame region to the outer portion of the substrate.

10. The device according to claim 1, wherein the nozzles are configured to release drops of liquid having a diameter smaller than 5 µm in response to activation of the heaters by the driving circuit.

11. The device according to claim 1, wherein the heaters are made of a material selected from the following group: polycrystalline silicon, Al, Pt, TiN, TiAlN, TaSiN, TiW.

12. The device according to claim 1, wherein the casing comprises a release mouthpiece and a housing that defines an internal chamber that receives the microfluidic cartridge in a removable way and communicates with the environment through the release mouthpiece.

13. The device according to claim 12, wherein the housing includes inlet holes in fluid communication with the internal chamber and wherein the inlet holes and the mouthpiece are arranged so that suction through the mouthpiece will draw air into the internal chamber through the inlet holes, passage of the air through the internal chamber, and subsequent release through the mouthpiece.

14. The device according to claim 1, wherein the nebulizer is one of a plurality of nebulizers of the microfluidic cartridge and the tank is one of a plurality of tanks of the microfluidic cartridge, the tanks being separated from each other and configured to contain respective liquids with respective distinct substances to be delivered, the tanks being fluidly coupled with the nebulizers, respectively.

15. A microfluidic cartridge comprising:

a tank configured to contain a liquid; and a nebulizer that includes:

a substrate;

a chamber layer on the substrate;

a plurality of supply passages fluidically coupled to the tank, the plurality of supply passages are concentric with each other;

a plurality of microfluidic channels in the chamber layer;

a plurality of chambers in a chamber layer and for receiving the liquid, the plurality of chambers are fluidically coupled to the plurality of supply passages by the plurality of microfluidic channels;

a plurality of heaters formed on the substrate in positions corresponding to the chambers, respectively, wherein the heaters are thermally coupled to the respective chambers, the heaters being configured to be controlled by the driving device;

an insulating layer separating the heaters from the respective chambers;

a plurality of nozzles fluidically connecting the chambers, respectively, to an environment outside of the nebulizer, wherein the chambers are delimited laterally by walls, and portions of surfaces of the walls extend through base areas of at least some of the nozzles;

a plurality of annular frame regions defined by the plurality of supply passages, the plurality of annular frame regions include respective portions of the substrate, of the insulating layer, and the chamber layer, and the plurality of annular frame regions are concentric with each other.

16. The microfluidic cartridge according to claim 15, wherein the supply passages are circular and concentric.

17. The microfluidic cartridge according to claim 15, wherein the nebulizer is one of a plurality of nebulizers of the microfluidic cartridge and the tank is one of a plurality of tanks of the microfluidic cartridge, the tanks being separated from each other and configured to contain respective liquids with respective distinct substances to be delivered, the tanks being fluidly coupled with the nebulizers, respectively.

18. A nebulizer comprising:

a substrate including:

a first frame region;

a second frame region;

an outer portion around the first and second frame regions;

an innermost supply passage arranged centrally within the first frame region;

a first outer supply opening separating the first and second frame regions from each other; and a second outer supply opening separating the second frame region from an outer portion of the substrate;

a plurality of chambers formed on the substrate and configured to receive a liquid;

a plurality of heaters formed on the substrate in positions corresponding to the chambers, respectively, wherein the heaters are thermally coupled to the respective chambers, the heaters being configured to be controlled by the driving device;

an insulating layer separating the heaters from the respective chambers;

a plurality of nozzles fluidically connecting the chambers, respectively, to an environment outside of the nebulizer, wherein the chambers are delimited laterally by walls, and portions of surfaces of the walls extend through base areas of at least some of the nozzles.

19. The nebulizer according to claim 18, further comprises:

a plurality of microfluidic channels and wherein the chambers are fluidically coupled to the supply passages, respectively, by the microfluidic channels, respectively.

20. The nebulizer according to claim 19, wherein the substrate includes:

a first bridge connecting the first and second frame regions to one another; and a second bridge connecting the second frame region to the outer portion of the substrate.

21. The nebulizer of claim 18, wherein the first and second frame regions include respective portions of the substrate and of the insulating layer.

22. The nebulizer of claim 18, wherein the first and second frame regions are concentric.

* * * * *